United States Patent
Chan et al.

(10) Patent No.: US 8,066,957 B2
(45) Date of Patent: Nov. 29, 2011

(54) EASY STRIP ACCESS PRIMARY CONTAINER AND METHODS OF MANUFACTURING AND UTILIZATION THEREOF

(75) Inventors: Frank A. Chan, Sunnyvale, CA (US); Chris Wiegel, Sunnyvale, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/646,167

(22) Filed: Dec. 23, 2009

(65) Prior Publication Data

US 2011/0147244 A1    Jun. 23, 2011

(51) Int. Cl.
*G01N 21/75* (2006.01)

(52) U.S. Cl. ........ 422/401; 422/547; 422/402; 422/310; 206/305; 206/755; 206/83; 206/535; 221/25; 221/229

(58) Field of Classification Search .................. None
See application file for complete search history.

(56) References Cited

U.S. PATENT DOCUMENTS

| | | | |
|---|---|---|---|
| 3,651,927 A * | 3/1972 | Richardson et al. .............. 221/5 |
| 4,231,624 A | 11/1980 | Neilsen |
| 4,906,057 A | 3/1990 | Davi et al. |
| 5,378,630 A | 1/1995 | Kai et al. |
| 5,505,308 A | 4/1996 | Eikmeier et al. |
| 5,720,924 A * | 2/1998 | Eikmeier et al. .............. 422/550 |
| 5,863,800 A | 1/1999 | Eikmeier et al. |
| 7,172,728 B2 | 2/2007 | Otake |
| 7,723,113 B2 * | 5/2010 | Charlton ........................ 436/46 |
| 2003/0185708 A1 | 10/2003 | Otake |
| 2006/0064035 A1 | 3/2006 | Wang et al. |
| 2007/0264166 A1 | 11/2007 | West et al. |

FOREIGN PATENT DOCUMENTS

| | | |
|---|---|---|
| EP | 1 855 110 A2 | 11/2007 |
| EP | 2 031 389 A1 | 3/2009 |

* cited by examiner

*Primary Examiner* — Sally Sakelaris
(74) *Attorney, Agent, or Firm* — Dinsmore & Shohl LLP

(57) ABSTRACT

Embodiments of the present invention relate to a test strip container which provides easy access to test strips. The test strip container includes a lower housing, an upper housing, and a retaining member configured to releasably retain the test strips in a nested configuration. The nested configuration of the test strip container provides easy access to test strips by arranging the test strips so that they extend radially outward from the retaining member. The radial arrangement of the test strips operates to separate the test strips so that test strip users may easily select a single test strip from a plurality of test strips. Alternatively, the test strip container includes a lower housing, an upper housing, and a retaining member configured to releasably retain the test strips in a longitudinal configuration.

12 Claims, 11 Drawing Sheets

EASY STRIP ACCESS PRIMARY CONTAINER AND METHODS OF MANUFACTURING AND UTILIZATION THEREOF

TECHNICAL FIELD

Embodiments of the present invention relate generally to test strip containers, and particularly to a primary container providing easy access to therein contained test strips and methods of manufacturing and utilization thereof.

BACKGROUND

The use of test strips in the determination of biological analyte concentration is of widespread importance, particularly to persons afflicted with type one diabetes. In regulating their disease, such diabetic patients may be required to perform an average of five to ten blood glucose tests per day via a process of self-monitoring to determine their blood glucose level. As a result, diabetic patients expend a significant amount of time throughout their daily lives testing their blood glucose levels.

As the number of patients suffering from diabetes increases, the practice of self-monitoring blood glucose levels has become routine. The process of self-monitoring typically involves diabetic patients obtaining a test strip, applying a sample of blood thereto, and obtaining results. Because the first step in the testing process is obtaining a test strip, the ability of diabetic person to easily obtain a test strip is of paramount importance.

Many difficulties associated with attaining a single test strip have been addressed at length in the prior art. For example, U.S. Pat. No. 7,172,728 mentions that the difficulties surrounding test strip retrieval stem from both the design of test strip storage containers and the physical capabilities of diabetic individuals. The configuration of many test strip containers is problematic in that they are commonly designed to store a plurality of test strips while protecting the test strips from contaminants. As a result, test strip containers commonly take the form of conventional vials.

In a conventional vial, test strips recess below the vial opening and must be manually removed. This configuration intuitively leads test strip users to dump the vial or turn the vial upside down to retrieve a single test strip. This process causes the test strips to spill onto the work surface or floor, and may result not only in contamination of the test strips but also in an extension of the period of time required for testing through the pick-up process. An alternative option to dumping the vial to attain a single test strip would be for test strip users to insert a finger into the vial to grasp a strip. This option is also imperfect in that this contact may result in either damage or contamination to the test strips remaining in the vial, leading to inaccurate blood glucose level results.

Another hindrance common to diabetic patients is limited physical dexterity. Persons with diabetes typically suffer from diminished hand-eye coordination, diminished finger sensation, or a combination of the two. As a result, the ability of persons afflicted with diabetes to pick up a single test strip from a plurality of test strips is limited. This problem is further enhanced by the fact that test strips are commonly only several millimeters in width and in length.

Some test strip containers have been designed to ease test strip users in the process of selecting a single test strip from amongst a plurality of test strips, see for example, U.S. Pat. No. 5,378,630, U.S. Pub. Nos. 2007/0264166 A1, 2007/0196240 A1, and 2003/0185708 A1. However these containers also carry with them a variety of disadvantages. Generally, the designs of the containers are more complex and not user friendly, diminishing the ease with which diabetic patients may operate the test strip containers.

SUMMARY

Embodiments of the present invention relate to a test strip container which provides easy access to test strips. The test strip container includes a lower housing, an upper housing, and a retaining member configured to releasably retain the test strips in a nested configuration. The nested configuration of the test strip container provides easy access to test strips by arranging the test strips so that they extend radially outward from the retaining member. The radial arrangement of the test strips operates to separate the test strips so that test strip users may easily select a single test strip from a plurality of test strips. Alternatively, the test strip container includes a lower housing, an upper housing, and a retaining member configured to releasably retain the test strips in a longitudinal configuration.

In one embodiment, a test strip container for providing ease of access to test strips provided therein is disclosed. The test strip container comprises a lower housing, an upper housing, and a retaining member. The retaining member is connected to the lower housing and is configured to releasably retain the test strips in a nested configuration wherein each of the test strips extends radially outward from the retaining member. Alternatively, the retaining member is configured to releasably retain the test strips in a longitudinal configuration wherein each of the test strips extends substantially normal to the retaining member. The test strip container has an open configuration and a closed configuration, wherein the uppermost test strips in the nested configuration are accessible in the open configuration, and wherein the test strips are concealed in the closed configuration.

In another embodiment, a test strip container for providing ease of access to test strips comprising a lower housing, an upper housing, and a retaining member is disclosed. The retaining member is configured to releasably retain the test strips in a nested configuration such that the test strips extend radially outward from the retaining member. The retaining member comprises a radial paddle structure having a plurality of members which extend radially outward from the center axle, and wherein the spaces between the plurality of members form a plurality of compartments such that the test strips may be placed within the plurality of compartments. The retaining member is connected to the lower housing and comprises a center axle substantially normal to the lower housing, wherein rotation of the center axle may result in rotation of the test strips. Additionally, the test strip container comprises an open configuration and a closed configuration wherein the upper test strips of the test strips are accessible in the open configuration and the test strips are concealed in the closed configuration.

In still another embodiment, a test strip container for providing ease of access to test strips comprising a lower housing, an upper housing, and a retaining member is disclosed. The retaining member is configured to releasably retain the test strips in a nested configuration such that the test strips extend radially outward from the retaining member. The retaining member comprises a test strip carrier structure comprising a disc and a center axle. The retaining member is connected to the lower housing and comprises a center axle substantially normal to the lower housing, wherein rotation of the center axle may result in rotation of the test strips. Additionally, the test strip container comprises an open configuration and a closed configuration wherein the upper test strips of the test strips are accessible in the open configuration and the test strips are concealed in the closed configuration.

In yet another embodiment, a method of manufacturing a test strip container for providing ease of access to test strips is disclosed. The method comprises providing a lower housing having surfaces which define a cavity for containing the test strips, providing an upper housing having surfaces which abut with the surfaces of the lower housing for enclosing the cavity, and providing a retaining member connected to the lower housing within the cavity and configured to releasably retain the test strips in a nested configuration wherein such of the test strips extends radially outward from the retaining member.

In still yet another embodiment, a method of providing easy access to test strips which comprises utilizing a test strip container according to the present invention is also disclosed.

These and other features and advantageous of these and other various embodiments according to the present invention will become more apparent in view of the drawings, detailed description, and claims provided that follow hereafter.

BRIEF DESCRIPTION OF THE DRAWINGS

The following detailed description of the embodiments of the present invention can be best understood when read in conjunction with the following drawings, where like structure is indicated with like reference numerals, and in which.

Skilled artisans appreciate that elements in the figures are illustrated for simplicity and clarity and have not necessarily been drawn to scale. For example, the dimensions of some of the elements in the figures may be exaggerated relative to other elements, as well as conventional parts removed, to help to improve understanding of the various embodiments of the present invention.

DETAILED DESCRIPTION

Embodiments of the present invention comprise a test strip container which provides easy access to a plurality of test strips held releasably therein. Each of the test strip container embodiments releasably retain the test strips generally enabling test strip users to easily select a single test strip from a plurality of test strips.

Figure 1:
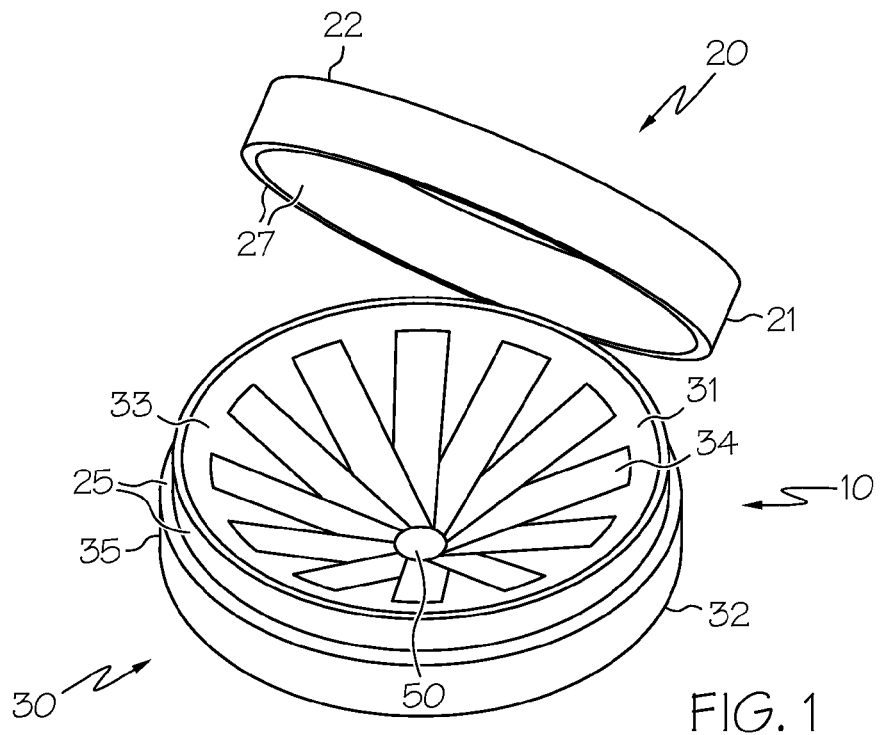
FIG. 1 is an upper perspective view of a container according to an embodiment of the present invention shown with upper and lower housings in an open configuration thereby providing easy access to test strips releasably held therein in a nested configuration according to the present invention.

FIG. 1 is an upper perspective view of a test strip container according to an embodiment of the present invention. As depicted in FIG. 1, the test strip container 10 comprises an upper housing 20, a lower housing 30, and a retaining member 50. The upper and lower housings 20, 30 are shown in an open configuration thereby providing easy access to test strips 34 shown provided therein. The retaining member 50 is configured to releasably retain the test strips 34 such that the test strips 34 may be released from the container 10 when a test strip user applies pressure to the test strips 34. In FIG. 1, the test strips 34 are releasably retained by the retaining member 50 in a nested configuration such that a plurality of test strips extend radially outward from the retaining member 50. As used herein, the term "nested configuration" refers to a configuration of the test strips wherein one portion of the test strips adhered to or accommodated by the retaining member overlap such that the test strips may extend outward from the retaining member.

For example, the nested configuration as depicted in FIG. 1, comprises an arrangement of test strips 34 wherein a portion of each test strip 34 may overlap with a portion of an adjacent test strip 34. In one embodiment the overlapping portions of adjacent test strips 34 may be releasably retained by the retaining member 50 via a biasing force applied by the retaining member 50 which releasably clamps, squeezes or holds the overlapping portions together. In another embodiment the overlapping portions of the test strips 34 may be releasably attached to a surface of the retaining member 50 by an adhesive.

Figure 1A:
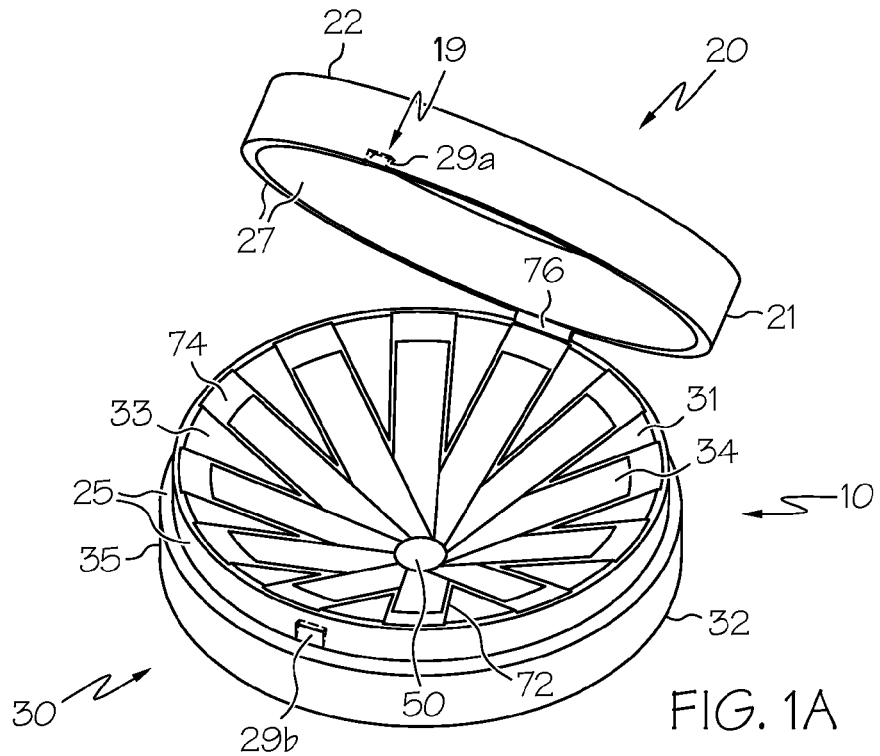
FIG. 1A is an upper perspective view of a container according to an embodiment of the present invention shown with upper and lower housings in an open configuration thereby providing easy access to test strips releasably held therein in a nested configuration according to the present invention.

In the illustrated embodiments depicted by FIGS. 1 and 1A, the nested configuration allows the test strips 34 to extend radially outward from the retaining member 50 such that they are not retained in a parallel configuration. Additionally, in these embodiments the nested configuration operates to separate the radially extending portions of the test strips 34 so that they may be easily accessed by test strip users. In a further embodiment of the nested configuration, the test strips 34 are releasably retained by the retaining member 50 in a nested configuration wherein the planar side of the test strips 34 rests substantially parallel to the lower housing 30. In one embodiment, the retaining member 50 connects to the lower housing 30 within the cavity 33 such that the test strips 34 are retained within the lower housing 30.

Figure 1B:
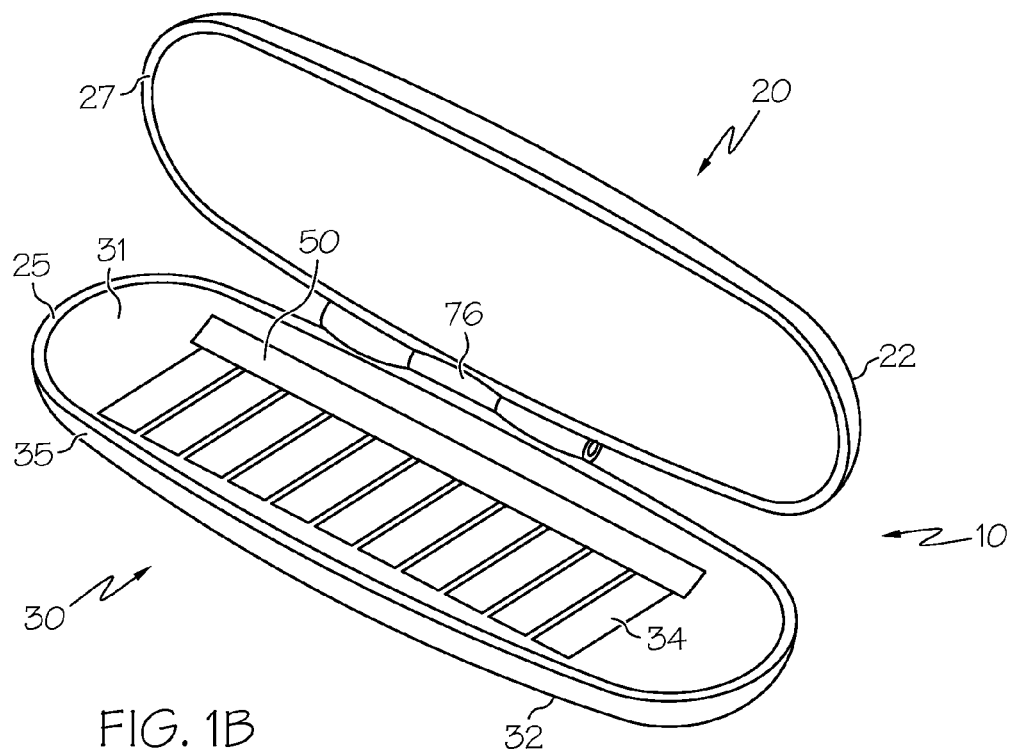
FIG. 1B is an upper perspective view of a container according to an embodiment of the present invention shown with upper and lower housing in an open configuration thereby providing easy access to test strips releasably held therein in a longitudinal configuration according to the present invention.

As depicted in FIGS. 1, 1A and 1B, the lower housing 30 has surfaces 25 which define a cavity 33 for containing test strips 34. In one embodiment, the upper housing 20 has surfaces 27 which may abut with the surfaces 25 of the lower housing 30 for enclosing the cavity 33. In another embodiment, the surfaces 25, 27 may mate to provide a releasable seal to form a protective environment for the test strips 34 provided in the container 10.

Figure 2:
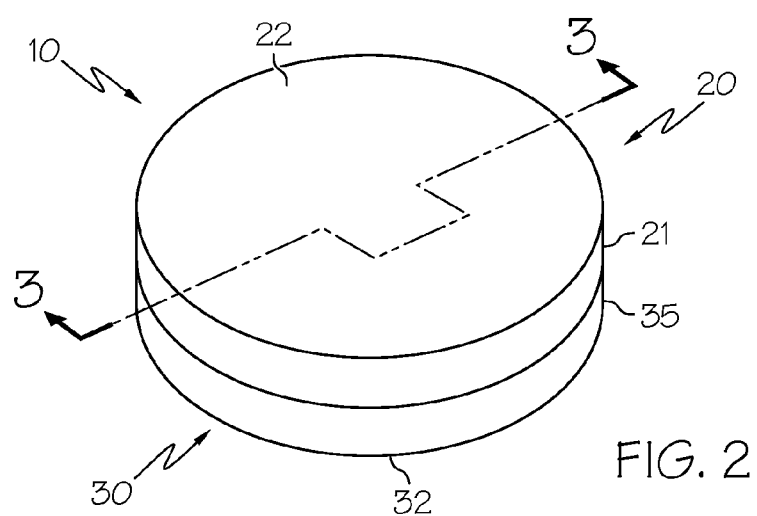
FIG. 2 is an upper perspective view of the container of FIG. 1 shown with the upper and lower housings in a closed configuration thereby concealing securely the test strips therein.
Figure 2A:
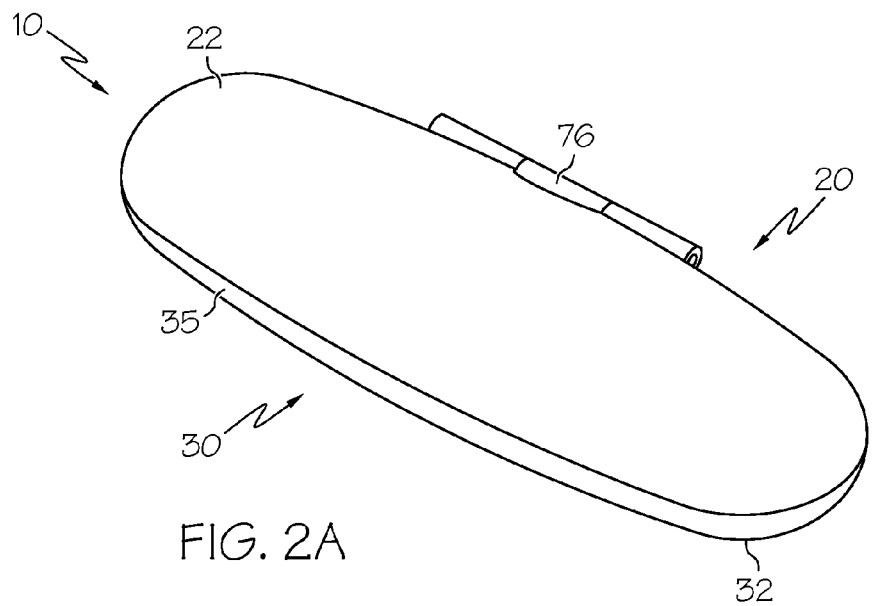
FIG. 2A is an upper perspective view of the container according of FIG. 1B shown with the upper and lower housings in a closed configuration thereby concealing securely the test strips therein.

The test strip container 10 comprises both an open configuration, as shown in FIGS. 1, 1A, and 1B, and a closed configuration, as shown in FIGS. 2 and 2A. The open configuration comprises the upper housing 20 being separated from the lower housing 30 wherein the uppermost test strips 34 are exposed. The exposed test strips 34 are accessible in the cavity 33 of the lower housing 30 to test strip users.

Figure 12:
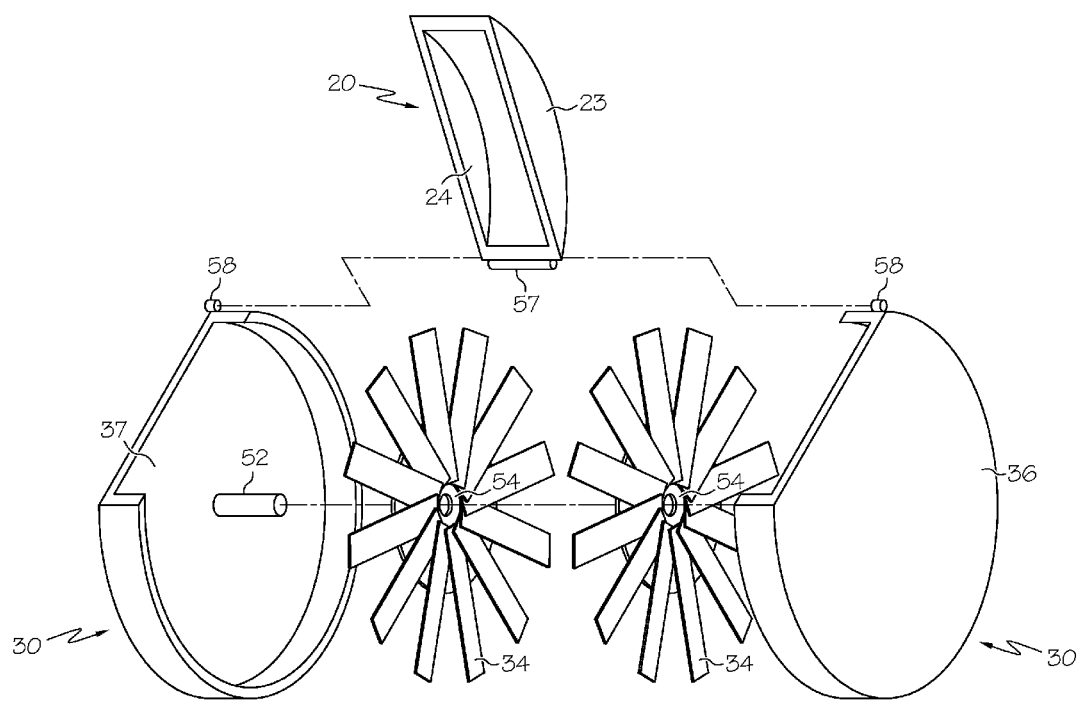
FIG. 12 is an exploded view of the container according to an embodiment of the present invention shown with upper and lower housings in an open configuration thereby providing easy access to test strips provided in an upright fan manner wherein a multiplicity of test strip carrier structures may be stacked within the cavity in the lower housing.

In one embodiment of the open configuration, the upper housing 20 may be hingedly attached to the lower housing 30 with a hinging mechanism 76. The hinging mechanism 76 in one embodiment may comprise a molded living hinge, such as depicted by FIGS. 1 and 1A. In this way, the upper housing 20 will not be wholly separated from the lower housing 30 in the open configuration. Rather, the upper housing 20 may pivot about the hinging mechanism 76 such that the uppermost test strips 34 are exposed within the cavity 33 of the lower housing 30. In another embodiment, the hinging mechanism 76 may comprise a pin 57 in a hole 58 arrangement, such as depicted by FIG. 12.

The closed configuration, as shown in FIGS. 2 and 2A, comprises the surfaces 25, 27 of the housings 20, 30 abutting to conceal the test strips 34 within the test strip container 10. In the closed configuration, test strips users may not access the test strips 34 within the test strip container 10. In this way, the closed configuration may be exploited to protect the test strips 34 within the test strip container 10 from moisture and other contaminants when the test strips 34 are not required for testing.

In one embodiment of the closed configuration, the test strip container 10 may optionally comprise a fastening mechanism 19 such that the test strip container 10 may be releasably fixed in the closed configuration. The fastening mechanism 19 in the embodiment illustrated by FIG. 1A is a latching mechanism comprising upper and lower releasably mating parts 29a, 29b, either mechanically or magnetically based, but in other embodiments, may include but is not limited thereto, a clamping mechanism or a snap-fit mechanism.

In one specific embodiment of the test strip container 10 as depicted in FIGS. 1, 1A, and 1B, the test strip container 10 may comprise a clamshell configuration. In the clamshell configuration, the upper housing 20 has surfaces including a side wall 21 and a top wall 22. The lower housing 30 also has surfaces including a side wall 35, an inner surface 31, and a bottom wall 32.

In one specific embodiment of the clamshell configuration, as depicted in FIG. 1B, the side wall 21 of the upper housing 20 and the side wall 35 of the lower housing 30 are substantially oblong and the top wall 22 of the upper housing 20 and the bottom wall 32 of the lower housing 30 are substantially flat. Thus, when in the closed configuration, as depicted in FIG. 2A, the test strip container 10 is substantially oblong with a substantially flat top wall 22 and bottom wall 32. In this particular embodiment, the retaining member 50 is substantially rectangular. The retaining member 50 retains releasably retains the test strips in a longitudinal configuration such that they extend substantially normal to the retaining member 50.

In an alternative embodiment of the clamshell configuration, as depicted in FIG. 1, the side wall 21 of the upper housing 20 and the side wall 35 of the lower housing 30 are substantially circular and the top wall 22 of the upper housing 20 and the bottom wall 32 of the lower housing 30 are substantially flat. In this particular embodiment, the retaining member 50 is substantially conical. Thus, when in the closed configuration, as depicted in FIG. 2, the test strip container 10 is substantially circular with a substantially flat top wall 22 and bottom wall 32.

In this particular embodiment of the clamshell configuration, the upper housing 20 may have a diameter slightly larger than the diameter of the lower housing 30 such that the side wall 21 of the upper housing 20 may overlap the side wall 35 of the lower housing 30 when in the closed configuration, creating an interference fit. In this way, test strip users must apply slight pressure to attain the open configuration. In an alternative embodiment, test strip users must apply a twisting force to the upper housing 20 such that it twists away from the lower housing 30 to attain the open configuration. In a further embodiment, the upper and lower housings 20, 30 may form together a moisture seal to protect the test strips from moisture and airborne debris.

Figure 3:
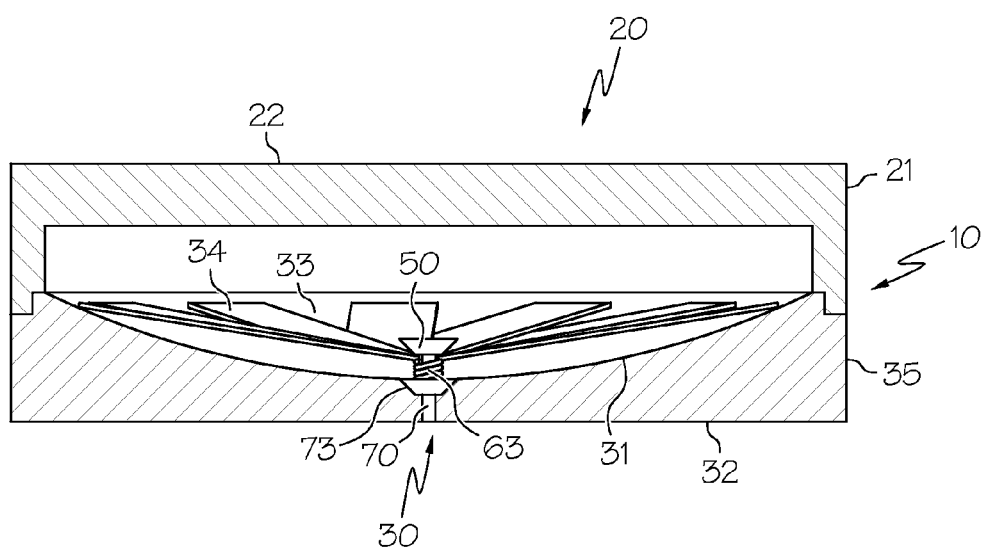
FIG. 3 is a section view taken along section line 3-3 depicted in FIG. 2 according to an embodiment of the present invention.

As shown in FIG. 3, the clamshell configuration also comprises the lower housing 30 having a concave interior. In this particular embodiment, the inner surface 31 of the lower housing 30 extends from the center of the bottom wall 32 of the lower housing 30 to the top of the side wall 35 of the lower housing 30. In this way, the inner surface 31 of the lower housing 30 will form an acute angle with the bottom wall 32 of the lower housing 30 such that the cavity 33 defined by the inner surface 31 of the lower housing 30 is concave.

The test strips 34 contained within the lower housing 30 will rest at an angle substantially congruent to or slightly greater than the concave interior of the lower housing 30. The angular arrangement of the test strips 34 provides test strip users with easy access to the test strips 34, as the test strips 34 may be slightly elevated from the concave interior of the test strip container 10.

In a further embodiment of the clamshell configuration as depicted in FIG. 3, the retaining member 50 which releasably retains the test strips 34 is substantially conical. The conical retaining member 50 forms an angle with the bottom wall 32 of the lower housing 30 that is substantially congruent to the concave interior of the inner surface 31 of the lower housing 30. As a result, the retaining member 50 fits complementarily within the concave interior of the lower housing 30. The retaining member 50 releasably retains test strips 34 in a nested configuration wherein the application of light pressure by the test strip user to the test strips 34 causes the retaining member 50 to release the test strips 34. The retaining member 50 may be attached to the lower housing 30 or may be accommodated by the lower housing 30.

Figures 3A, 3B:
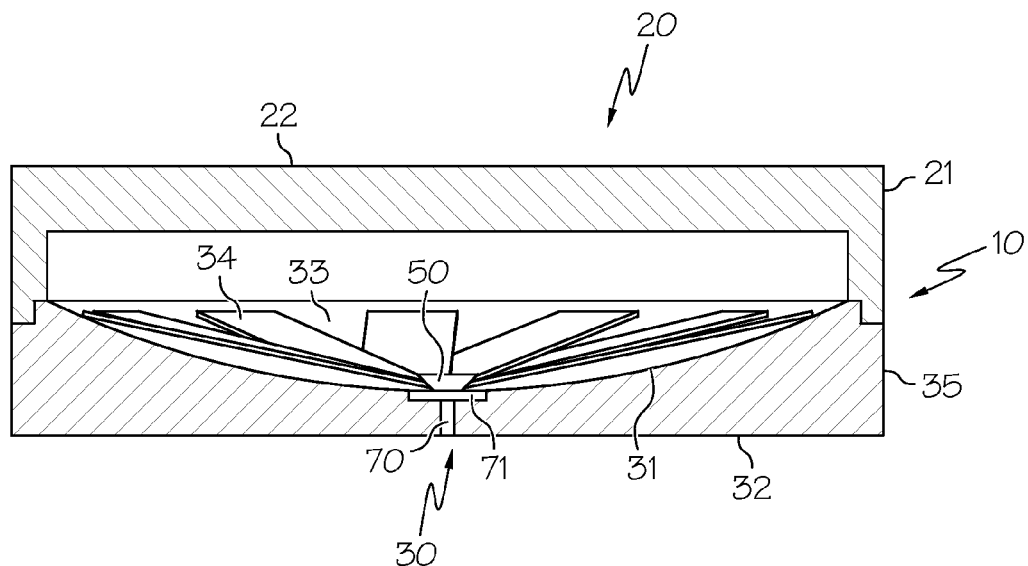
FIG. 3A is a section view taken along section line 3-3 depicted in FIG. 2 according to another embodiment of the present invention.
FIG. 3B is a section view taken along section line 3-3 depicted in FIG. 2 according to another embodiment of the present invention.
Figure 11:
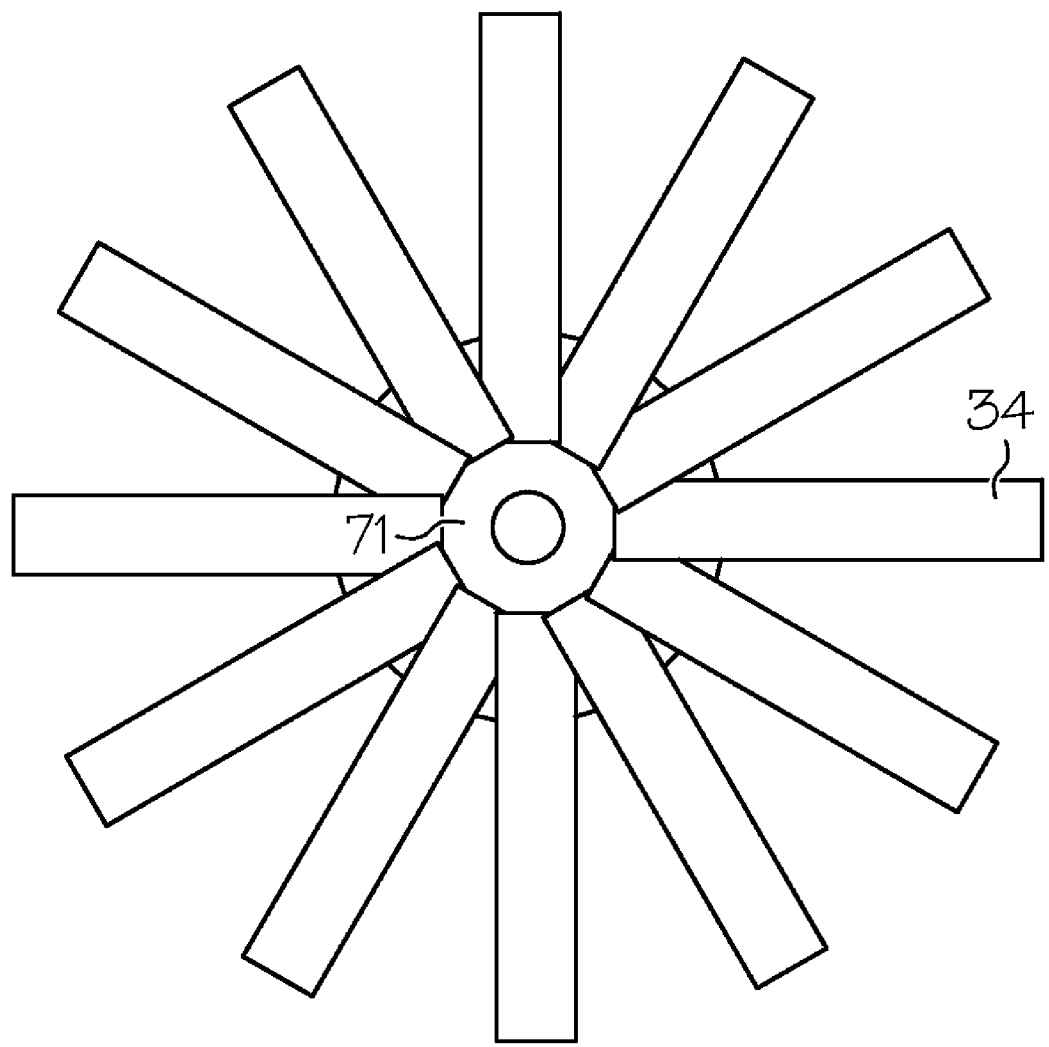
FIG. 11 is a front view of the test strips attached to an adhesive disc in a nested configuration according to an embodiment of the present invention.

In one specific embodiment of the clamshell configuration, the retaining member 50 is a static retainer. As depicted in FIG. 3A, in this particular embodiment, the retaining member 50 is attached to a locking peg 70. In this specific embodiment, the test strips 34 are attached to an adhesive disc 71 in a nested configuration, as depicted in FIG. 11. The test strips 34 are attached to the adhesive disc 71 such that one end of the test strips 34 are adhered to the adhesive disc 71. The retaining member 50 serves to anchor the adhesive disc 71 within the lower housing 30. The locking peg 70 is arranged substantially within the center of the bottom wall 32 of the lower housing 30. In this embodiment, the retaining member 50 snaps onto the locking peg 70. In an alternative embodiment, the locking peg 70 may be integral with the bottom wall 32 of the lower housing 30 as a molded portion thereof or overmolded thereby.

In an alternative embodiment of the clamshell configuration, the lower housing 30 has a plurality of ridges 72, as depicted in FIG. 1A. The plurality of ridges 72 are arranged in a nested configuration or a longitudinal configuration such that the test strips 34 may be loaded directly into the lower housing 30 between the plurality of ridges 72. The plurality of ridges 72 are arranged such that the gap distance between each ridge is approximately equal to the width of the test strips 34. In accordance with this specific embodiment, as depicted in FIG. 3A, the retaining member 50 is a static retainer that is substantially conical. In an alternative embodiment, the retaining member 50 is substantially rectangular. In one embodiment, the retaining member 50 may be over molded. In a further embodiment, a multiplicity of test strips 34 may be loaded directly into the lower housing 30 between the plurality of ridges 72 wherein a multiplicity of test strips 34 are placed on top of one another.

In an alternative embodiment, as depicted in FIG. 3B, the retaining member 50 fits complementarily within a compliant washer 73. The compliant washer 73 comprises a compressible material. The compressible material may include but should not be limited to foam, rubber, and other elastomers. The compliant washer 73 snaps onto a locking peg 70 arranged within the lower housing 30 such that it is arranged substantially within the center of the bottom wall 32. The compliant washer 73 serves to compress the test strips 34 against the bottom wall 32 of the lower housing 30, providing sufficient friction to anchor the test strips 34 within the lower housing 30. In this specific embodiment, the lower housing 30 possesses a detent 74 which extends around the circumference of the lower housing 30. The detent 74, as depicted in FIG. 1A, allows for easy access to the test strips 34.

In an alternative embodiment of the clamshell configuration, the retaining member 50 is a dynamic retainer that is substantially conical. In another embodiment, the retaining member 50 is substantially rectangular. As depicted in FIG. 3, the retaining member 50 is spring-biased towards the inner surface 31 of the lower housing 30 in this particular embodiment. In this particular embodiment, a spring 63 has one end attached to the retaining member 50 and an opposing end attached to a compliant washer 73. The compliant washer 73 snaps onto a locking peg 70 arranged within the lower housing 30 such that it is arranged substantially within the center of the bottom wall 32.

In this particular embodiment, a multiplicity of test strips 34 may be stacked on top of one another. Removal of the test strips 34 on the top of the multiplicity of test strips 34 results in the spring 63 pulling under retraction. When the spring 63 pulls under retraction, the retaining member 50 translates downwardly toward the compliant washer 73 and the locking peg 70. The translation of the retaining member 50 results in the test strips 34 previously residing underneath the test strips 34 that were on the top layer of the stack to pivot vertically away from the concave surface of the cavity 33 due to the cone shape of the retaining member 50 moving downwardly centrally about the retained ends of the remaining test strips 34. Such a configuration thus allows test strip users to acquire a test strip easily from the multiplicity of layers of test strips contained within the test strip container 10 via the rising feature of each test strip.

In one specific embodiment of the clamshell configuration, the test strip container 10 may comprise a configuration wherein the test strips 34 are releasably stacked on top of one another. In this way, the test strips 34 releasably retained by the retaining member 50 in a nested configuration and extending radially outward from the retaining member 50 are arranged such that a multiplicity of test strips 34 are placed on top of one another.

In this way, a multiplicity of layers of test strips 34 may be contained within one test strip container 10. Where the test strips 34 are stacked, test strip users may obtain a test strip 34 from the multiplicity of test strips which are releasably retained on the top layer of the stack. In a further embodiment of the stacked configuration, the retaining member 50 may be spring-biased as previously discussed above and as shown in FIG. 3.

Figure 4:
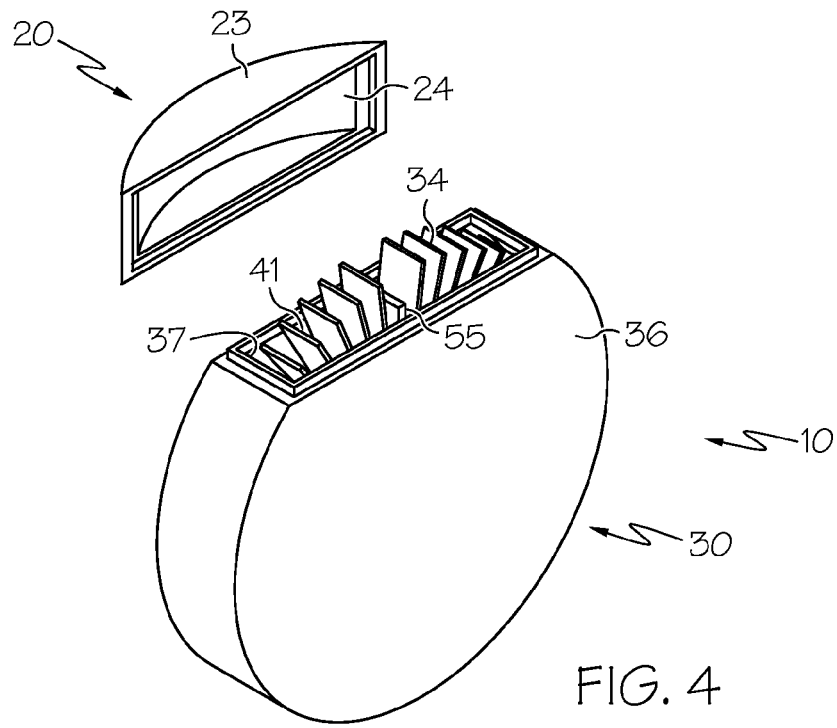
FIG. 4 is an upper side perspective view of a container according to another embodiment of the present invention shown with upper and lower housings in an open configuration thereby providing easy access to test strips provided in an upright file manner and releasably attached at an end about a rotatable central axle according to the present invention.

In an alternative embodiment of the test strip container 10, the test strip container 10 may comprise a rolodex-type configuration, as shown in FIG. 4. In the rolodex-type configuration, the lower housing 30 of the test strip container 10 has an outer surface 36 and an inner surface 37 which define a cavity 33 for containing the test strips 34. The lower housing 30 of the rolodex-type configuration comprises an aperture 41 defined by the lower housing 30 through which the plurality of test strips 34 may extend. The upper housing 20 has an outer surface 23 and an inner surface 24 such that the outer surface 23 and the inner surface 24 of the upper housing 20 abut with the outer surface 36 and the inner surface 37 of the lower housing 30 enclosing the cavity 33.

As shown in FIG. 4, the upper and lower housings 20, 30 may comprise an open configuration thereby providing easy access to the test strips 34 provided in an upright file manner and releasably attached at an end about a rotatable center axial member.

Figure 5:
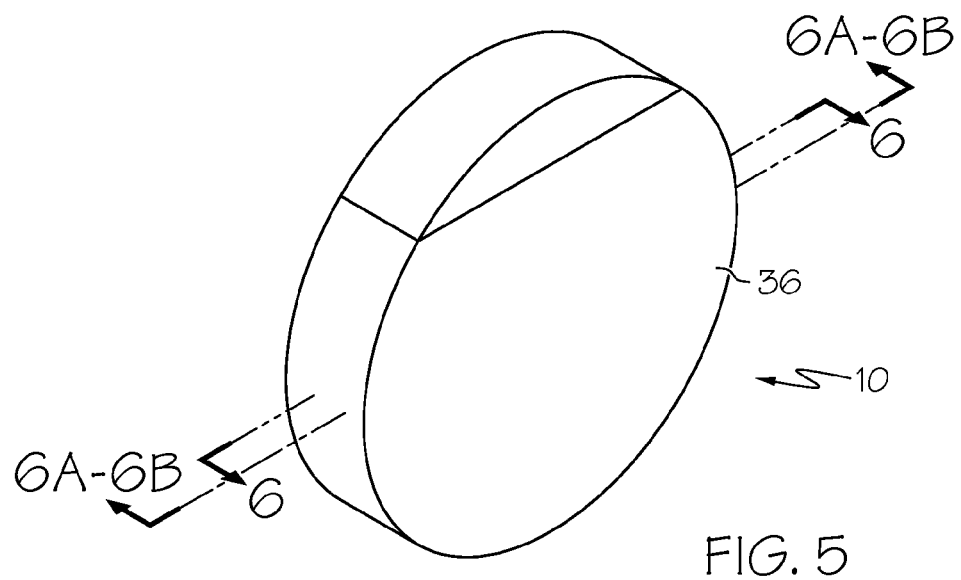
FIG. 5 is an upper side perspective view of the container of FIG. 5 shown with the upper and lower housings in a closed configuration thereby concealing securely the test strips therein.

In one particular embodiment of the rolodex-type configuration, the lower housing 30 is substantially circular with an angled aperture 41 defined by the lower housing 30, and the upper housing 20 is substantially semi-circular, such that the upper housing 20 coordinates with the angled aperture 41 defined by the lower housing 30 to form a substantially circular test strip container 10 in the closed configuration shown in FIG. 5.

Figure 6:
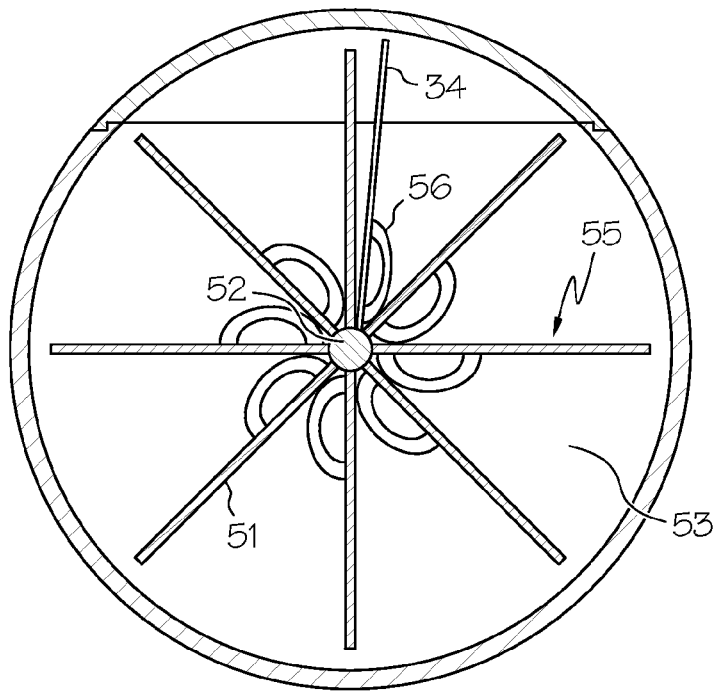
FIG. 6 is a section view taken along section line 6-6 depicted in FIG. 5.

The retaining member 50 of the rolodex-type configuration is housed within the lower housing 30. The retaining member 50 is configured to releasably retain the test strips 34 in a nested configuration. The retaining member 50 is a radial paddle structure 55 having a plurality of paddle members 51, as depicted in FIG. 6. The retaining member 50 comprises a center axle 52 which is substantially normal to the lower housing 30 and which extends through the retaining member 50 in the lower housing 30. The retaining member 50 is connected to the lower housing 30 within the cavity 33 and is configured to releasably retain the test strips 34.

The plurality of paddle members 51 of the radial paddle structure 55 extend radially outward from the center axle 52. The radial paddle structure 55 is connected to the lower housing 30 within the cavity 33 and is configured to releasably retain the test strips 34 in a nested configuration wherein such of the test strips 34 extends radially outward from the retaining member 50. The radial paddle structure 55 snaps onto the center axle 52 in the lower housing 30. The plurality of paddle members 51 of the radial paddle structure 55 extend radially outward. The spaces in between the plurality of members 51 form a plurality of compartments 53 such that the test strips 34 may be placed within the plurality of compartments 53. The plurality of paddle members 51 of the radial paddle structure 55 extend slightly above the angled aperture 41 defined by the lower housing 30 such that the length of the plurality of paddle members 51 is less than the length of the test strips 34 along their longitudinal axis. In this way, a test strip user may grasp one of the plurality of paddle members 51 through the angled aperture 41 defined by the lower housing 30 and manually rotate the radial paddle structure 55 to the next of the plurality of compartments 53.

The nested configuration, as depicted in FIG. 6, comprises an arrangement of test strips 34 wherein a portion of each test strip 34 may overlap with a portion of another test strip 34. The overlapping portions are accommodated by the radial paddle structure 55 in the rolodex-type configuration. The nested configuration allows the test strips 34 to extend radially outward from the retaining member 50 such that they are not retained in a parallel configuration. In one specific embodiment of the rolodex-type configuration, as depicted in FIG. 6, a leaf spring 56 is added to each of the plurality of compartments 53 such that the test strips 34 may be retained within the radial paddle structure 55. In a further embodiment of the nested configuration, the test strips 34 are releasably retained by the radial paddle structure 55 in a nested configuration wherein the planar side of the test strips 34 rests substantially parallel to the plurality of members 51.

Figure 6A:
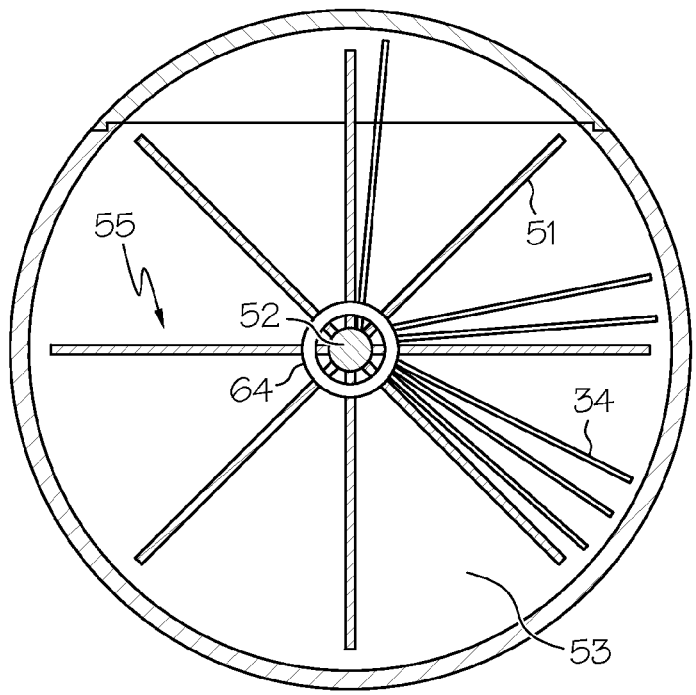
FIG. 6A is a section view taken along section line 6A-6A depicted in FIG. 5 shown with the test strips held within the retaining member via an adhesive film.

In one embodiment of the rolodex configuration, the test strips 34 are retained within the radial paddle structure 55 with a retention feature such as a foam or an adhesive film. An adhesive retainer 64 is depicted in FIG. 6A. Alternatively, the test strips 34 are accommodated by the radial paddle structure 55 by placing the test strips loosely within the plurality of compartments 53.

Rotation of the center axle 52 by the test strip user may result in rotation of the retaining member 50 such that the test strips 34 releasably retained by the radial paddle structure 55 may be rotated and accessed through the aperture 41 defined by the lower housing 30. In a further embodiment of the rolodex-type configuration, access to test strips 34 through the aperture 41 defined by the lower housing 30 may optionally be improved by angling the aperture 41 defined by the lower housing 30 such that test strips 34 may extend through a larger area. An optional feature of the rolodex-type configuration is a unidirectional advancement mechanism 60 wherein rotation of the center axle 52 is restricted to one direction.

In one specific embodiment of the rolodex-type configuration, the plurality of compartments 53 in the radial paddle structure 55 may be sealed by adding a sealing material to the inner surface 37 of the lower housing 30 which the plurality of members 51 contact. Additionally, an alternative embodiment comprises sealing the plurality of compartments 53 by over molding. Sealing the plurality of compartments 53 by over molding may comprise the use of but should not be limited to thermoplastic elastomers (i.e. TPE), rubber, or flexible polymers.

Figure 7:
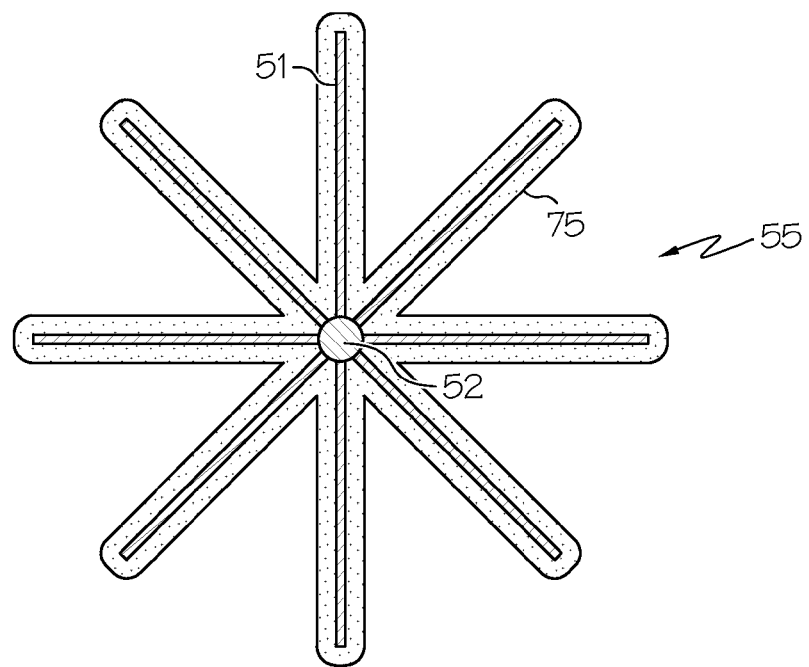
FIG. 7 is a front view of a radial paddle structure over molded with TPE according to an embodiment of the present invention.

In one particular embodiment, the plurality of compartments 53 are sealed by over molding with TPE 75, as depicted in FIG. 7. The over-mold is applied on the contact edge of the radial paddle structure 55 wherein contacting the inner surface 37 of the lower housing 30 and permitting rotation of the radial paddle structure 55. The over-mold applied on the contact edge of the radial paddle structure 55 may comprise a lip seal, i.e. a wiper blade type seal. The over-mold serves as a gasket between the radial paddle structure 55 and the inner surface 37 of the lower housing 30 such that the plurality of compartments 53 are secured from any contaminants that may be encountered while the test strip container 10 is in the open configuration. More particularly, any contaminants encountered while the test strip container 10 is in the open configuration will be confined to the plurality of compartments 53 exposed in the open configuration.

Figure 6B:
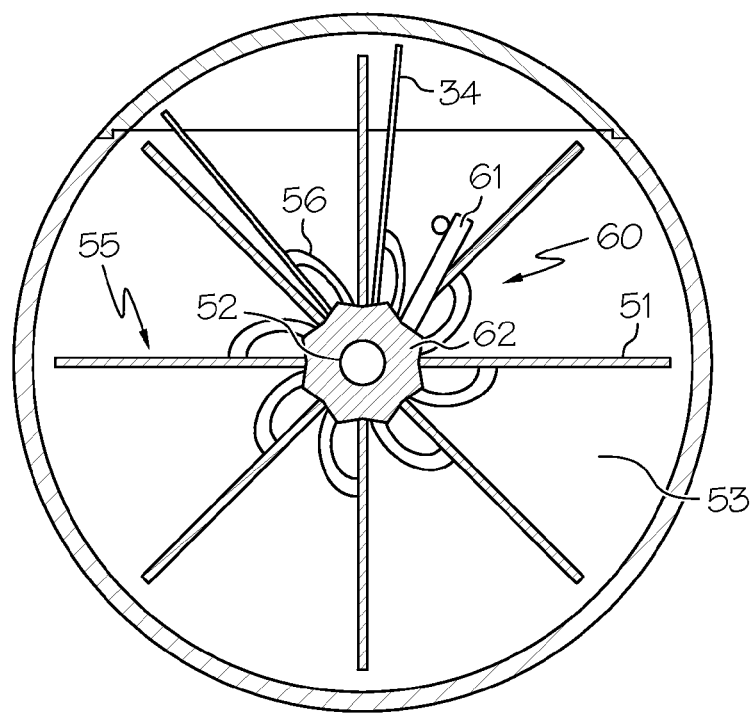
FIG. 6B is a section view taken along section line 6B-6B depicted in FIG. 5 shown with a unidirectional advancement mechanism.

Another optional feature of the rolodex-type configuration is a unidirectional advancement mechanism 60 which would operate to restrict rotation of the center axle 52 to one direction. In one specific embodiment, the unidirectional advancement mechanism is a pawl 61 and ratchet 62 as shown in FIG. 6B. In this particular embodiment, the ratchet 62 is affixed to the radial paddle structure 55 such that it rotates with the radial paddle structure 55. In this way, the pawl 61 may engage the ratchet 62, therein restricting the rotation of the radial paddle structure 55 to one direction.

Figure 8:
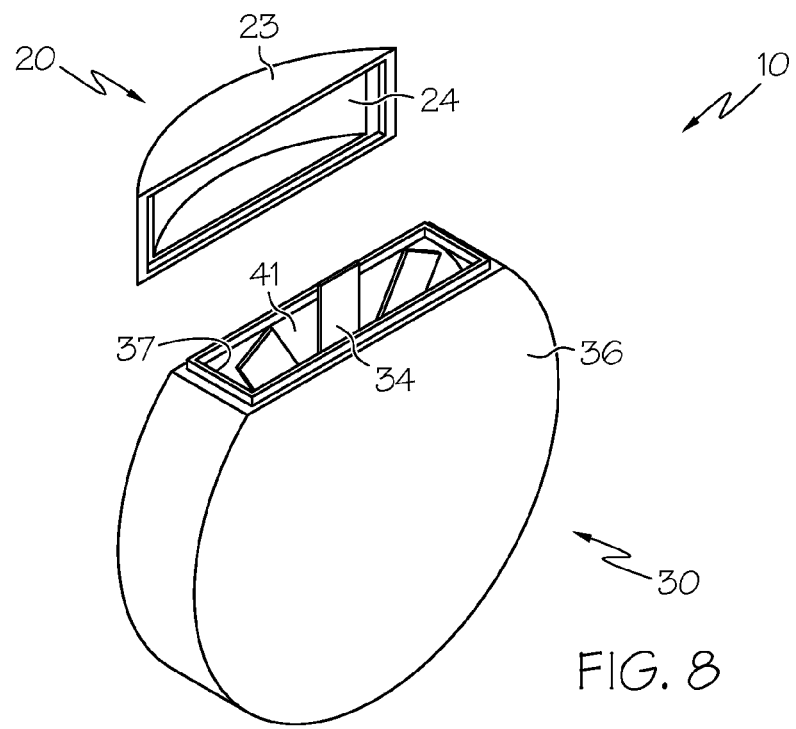
FIG. 8 is an upper side perspective view of a container according to still another embodiment of the present invention shown with upper and lower housings in an open configuration thereby providing easy access to test strips provided in an upright fan manner and releasably attached at an end about a rotatable central axle [[axel]] according to the present invention.

In an alternative embodiment of the test strip container 10, the test strip container 10 may comprise a pinwheel configuration as depicted in FIG. 8. In the pinwheel configuration, the lower housing 30 of the test strip container 10 has an outer surface 36 and an inner surface 37 which define a cavity 33 for containing the test strips 34. The lower housing 30 of the pinwheel configuration comprises an aperture 41 defined by the lower housing 30 through which the plurality of test strips 34 may extend. The upper housing 20 has an outer surface 23 and an inner surface 24 such that the outer surface 23 and the inner surface 24 of the upper housing 20 abut with the outer surface 36 and the inner surface 37 of the lower housing 30 for enclosing the cavity 33.

As shown in FIG. 8, the upper and lower housings 20, 30 may comprise an open configuration thereby providing easy access to the test strips 34 provided in an upright fan manner and releasably attached at an end about a rotatable center axle 52.

Figure 9:
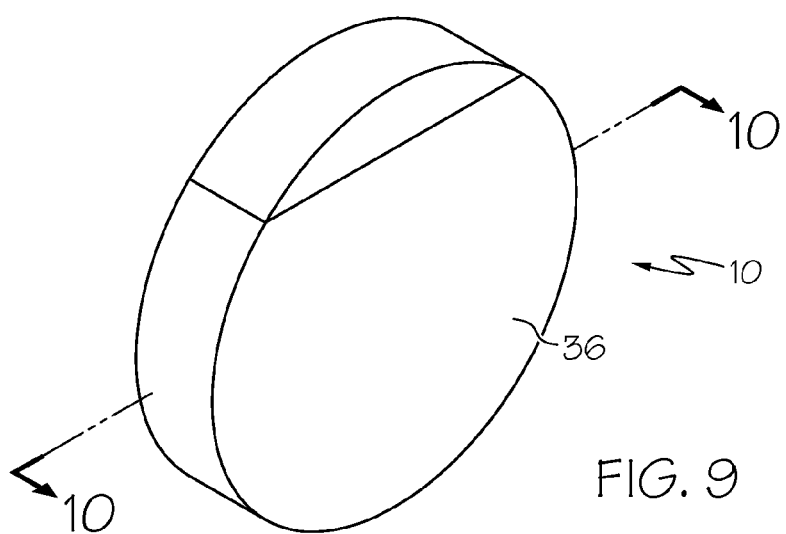
FIG. 9 is an upper side perspective view of the container of FIG. 7 shown with the upper and lower housings in a closed configuration thereby concealing securely the test strips therein.

In one particular embodiment of the pinwheel configuration, the lower housing 30 is substantially circular with an angled aperture 41 defined by the lower housing 30, as depicted in FIG. 8. The upper housing 20 is substantially semi-circular, such that the upper housing 20 coordinates with the angled aperture 41 defined by the lower housing 30 to form a substantially circular test strip container 10 in the closed configuration as shown in FIG. 9.

Figure 10:
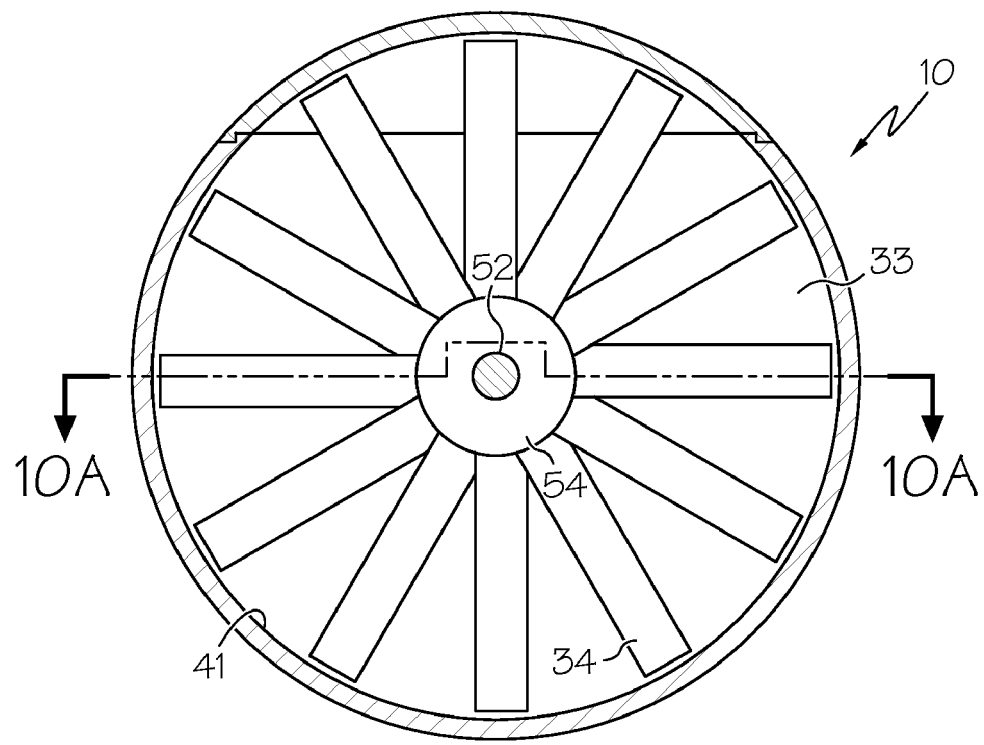
FIG. 10 is a section view taken along section line 10-10 depicted in FIG. 9.

As shown by FIG. 10, the retaining member 50 of the pinwheel configuration is housed within the lower housing 30. The retaining member 50 is configured to releasably retain the test strips 34 in a nested configuration. The retaining member 50 is a test strip carrier structure comprising a center axle 52 and a disc 54. The center axle 52 is substantially normal to the lower housing 30 and extends through the retaining member 50 in the lower housing 30. The retaining member 50 is connected to the lower housing 30 within the cavity 33 and is configured to releasably retain the test strips 34.

The disc 54 of the pinwheel configuration is substantially planar having a diameter smaller than the length of the test strips 34, see FIG. 10. The disc 54 is arranged within the cavity 33 of the lower housing 30 such that the planar side of the disc 54 is substantially parallel to the inner surface 37 of the lower housing 30 wherein the test strips 34 may be adhered.

Figure 10A:
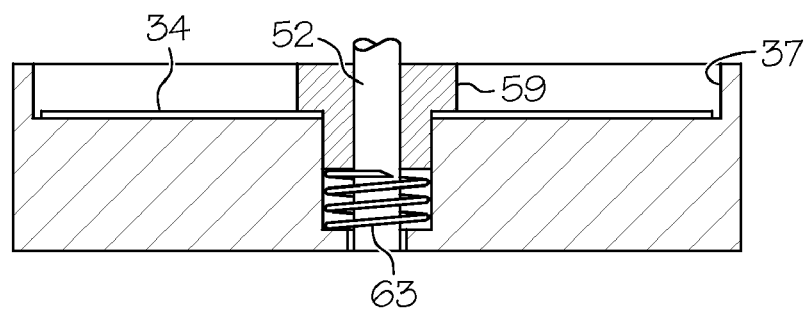
FIG. 10A is a section view taken along section line 10A-10A depicted in FIG. 10 shown with a retaining clip.

In an alternative embodiment of the pinwheel configuration, the test strips may be adhered to the disc 54 with a retaining clip 59 which is spring-biased, as shown in FIG. 10A. In a further embodiment, a spring 63 is connected to the retaining clip 59 such that the retaining clip 59 retains the test strips 34. In one particular embodiment, the spring 63 pulls the retaining clip 59 under retraction such that the retaining clip 59 translates toward the spring 63 in a direction parallel to the center axle 52. In an alternative embodiment, the spring 63 pushes the retaining clip 59 under expansion such that the retaining clip 59 translates toward the spring 63 in a direction parallel to the center axle 52.

In still another embodiment, the test strips may be adhered to the disc 54 with a light adhesive or with clips. In one specific embodiment, as depicted in FIG. 11, the disc 54 may be an adhesive disc 71, wherein the test strips 34 are adhered. In a further embodiment of the pinwheel configuration, the test strips 34 are adhered to the disc 54 in a nested configuration wherein the planar side of the test strips 34 rests substantially parallel to the planar side of the disc 54. In one particular embodiment of the pinwheel configuration, a multiplicity of test strip carrier structures may be stacked within the cavity 33 in the lower housing 30. In this stacked configuration, for example as depicted by FIG. 12, a plurality of discs 54 may be arranged within the lower housing 30 such that the center axle 52 extends through the plurality of discs 54. Rotation of the center axle 52 by the test strip user may result in rotation of the disc 54 such that the test strips 34 adhered to the disc 54 may also be rotated and accessed through the aperture 41 defined by the lower housing 30. In a further embodiment of the pinwheel configuration, access to test strips 34 through the aperture 41 may optionally be improved by angling the aperture 41 such that test strips 34 may extend through a larger area.

In yet another embodiment, a method of manufacturing a test strip container 10 for providing ease of access to test strips 34 is disclosed. The method comprises providing a lower housing 30 having surfaces which define a cavity 33 for containing the test strips 34, providing an upper housing 20 having surfaces which abut with the surfaces of the lower housing 30 for enclosing the cavity 33, and providing a retaining member 50 connected to the lower housing 30 within the cavity 33 and configured to releasably retain the test strips 34 in a nested configuration wherein such of the test strips 34 extends radially outward from the retaining member 50.

In still yet another embodiment, a method of providing easy access to test strips 34 which comprises utilizing a test strip container 10 according to the present invention is also disclosed.

The above description and drawings are only to be considered illustrative of exemplary embodiments, which achieve the features and advantages of the present invention. Modification and substitutions the features and steps described can be made without departing from the intent and scope of the present invention. Accordingly, the invention is not to be considered as being limited by the foregoing description and drawings, but is only limited by the scope of the appended claims.

What is claimed is:

1. A test strip container for providing ease of access to test strips comprising:
    a lower housing having surfaces which define a cavity for containing the test strips;
    an upper housing having surfaces which abut with the surfaces of the lower housing for enclosing the cavity; and
    a retaining member connected to the lower housing within the cavity and configured to releasably retain the test strips wherein each of the test strips extends outwardly from the retaining member, wherein the test strips are radially overlapping and in contact with adjacent ones thereof, and wherein the test strip container has an open configuration and a closed configuration, in which:
        the open configuration comprises the upper housing being separated from the lower housing wherein the test strips are accessible in the cavity of the lower housing, and
        the closed configuration comprises the surfaces of the upper housing and the lower housing abutting to conceal the test strips within the test strip container.

2. The test strip container of claim 1, wherein the upper housing and the lower housing are substantially circular.

3. The test strip container of claim 2, wherein the test strips are retained in a nested configuration wherein each of the test strips extends radially outward from the retaining member.

4. The test strip container of claim 3, wherein the cavity of the lower housing is a concave interior.

5. The test strip container of claim 4, wherein the test strips rest at an angle substantially congruent to the concave interior of the lower housing.

6. The test strip container of claim 5, wherein the retaining member is substantially conical having an angle substantially congruent to the concave interior of the lower housing.

7. The test strip container of claim 6, wherein the test strips are arranged such that a multiplicity of test strips are placed on top of one another.

8. The test strip container of claim 1, wherein the upper housing and the lower housing are substantially oblong.

9. The test strip container of claim 8, wherein the retaining member is substantially rectangular.

10. The test strip container of claim 9, wherein the test strips are retained in a longitudinal configuration such that they extend substantially normal to the retaining member.

11. A method of manufacturing a test strip container for providing easy access to test strips, comprising:
    providing a lower housing having surfaces which define a cavity for containing the test strips;
    providing an upper housing having surfaces which abut with the surfaces of the lower housing for enclosing the cavity; and
    providing a retaining member connected to the lower housing within the cavity and configured to releasably retain the test strips in a nested configuration wherein such of the test strips extends radially outward from the retaining member and wherein the test strips are radially overlapping and in contact with adjacent ones thereof.

12. A method of providing easy access to test strips which comprises utilizing the test strip container of claim 1.

* * * * *

UNITED STATES PATENT AND TRADEMARK OFFICE
CERTIFICATE OF CORRECTION

| | | |
|---|---|---|
| PATENT NO. | : 8,066,957 B2 | Page 1 of 1 |
| APPLICATION NO. | : 12/646167 | |
| DATED | : November 29, 2011 | |
| INVENTOR(S) | : Frank A. Chan et al. | |

It is certified that error appears in the above-identified patent and that said Letters Patent is hereby corrected as shown below:

Col. 3, Line 17, features and advantageous -- should read -- features and advantages Col. 3, Line 50, according of -- should read -- according to Col. 6, Line 28, member 50 retains releasably -- should read -- member 50 releasably retains Col. 12, Line 2, substitutions the features -- should read -- substitutions of the features Signed and Sealed this
Twenty-fourth Day of April, 2012

David J. Kappos
*Director of the United States Patent and Trademark Office*